US008219325B2

(12) United States Patent
Lehmann (10) Patent No.: US 8,219,325 B2
(45) Date of Patent: Jul. 10, 2012

(54) METHOD FOR DETERMINING THE RATIO OF TWO DISTINCT PEPTIDES OR POLYNUCLEIC ACIDS

(75) Inventor: Wolf Dieter Lehmann, Heidelberg (DE)

(73) Assignee: DKFZ Deutsches Krebsforschungszentrum Stiftung Des Offentlichen Rechts, Heidelberg (DE)

( * ) Notice: Subject to any disclaimer, the term of this patent is extended or adjusted under 35 U.S.C. 154(b) by 679 days.

(21) Appl. No.: 12/226,598

(22) PCT Filed: Apr. 25, 2007

(86) PCT No.: PCT/EP2007/054054
§ 371 (c)(1), (2), (4) Date: Jan. 14, 2009

(87) PCT Pub. No.: WO2007/122250
PCT Pub. Date: Nov. 1, 2007

(65) Prior Publication Data
US 2010/0015609 A1 Jan. 21, 2010

(30) Foreign Application Priority Data
Apr. 26, 2006 (EP) .................................... 06113151

(51) Int. Cl.
*G01N 33/48* (2006.01)
*G01N 33/50* (2006.01)

(52) U.S. Cl. .......................................... 702/19; 702/20

(58) Field of Classification Search .................. None
See application file for complete search history.

(56) References Cited

U.S. PATENT DOCUMENTS
2004/0119010 A1 6/2004 Perryman et al.

FOREIGN PATENT DOCUMENTS
WO WO-99/03872 1/1999

OTHER PUBLICATIONS

Kruger et al., "Protein and Proteome Phosphorylation Stoichiometry Analysis by Element Mass Spectrometry," Anal. Chem. Mar. 2006 (available online with a publication date of Feb. 14, 2006), vol. 78, pp. 1987-1994.*
Steen, Hanno et al. "Stable isotope-free relative and absolute quantitation of protein phosphorylation stoichiometry by MS." PNAS, Mar. 15, 2005, vol. 102, No. 11, pp. 3948-3953. XP-002396491.
Ruse, Christian I. et al. "Quantitative Dynamics of Site-Specific Protein Phosphorylation Determined Using Liquid Chromatography Electrospray Ionization Mass Spectrometry" Analytical Chemistry, vol. 74, No. 7, Apr. 1, 2002.

* cited by examiner

*Primary Examiner* — Jason Sims
(74) *Attorney, Agent, or Firm* — Birch, Stewart, Kolasch & Birch, LLP (57) ABSTRACT

The invention relates to a method for determining the ratio of two distinct target-peptides or polynucleic acids comprising: a) obtaining a sample containing said two distinct target-peptides or polynucleic acids, b) providing a precursor-peptide or precursor-polynucleic acid, comprising the two distinct target-peptides or -polynucleic acids in a known ratio, wherein the two distinct target-peptides or -polynucleic acids are connected by a cleavage site, c) cleaving the precursor-peptide or precursor-polynucleic acid at the cleavage site to obtain a standard with the known ratio of the two distinct target-peptides or -polynucleic acids, d) detecting a signal of each distinct target-peptide or -polynucleic acid of the standard in an analyzer, comparing the signals with the known ratio and determining a correction factor, e) detecting the signal of each distinct target-peptide or -polynucleic acid of the sample in the analyzer and f) determining the ratio of the two distinct target-peptides or -polynucleic acids by means of the correction factor or by double ratio calculation (calculation of the ratio of two intensity ratios—namely of the peptide and isoform-peptide with their corresponding labelled standards) to eliminate the compound-specific correction factors.

13 Claims, 6 Drawing Sheets

SEQUENCE LISTING

<160> NUMBER OF SEQ ID NOS: 19

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 1

Gly Ser Thr Ala Glu Asn Ala Glu Tyr Leu Arg

```
1               5                   10
```

<210> SEQ ID NO 2
<211> LENGTH: 11
<212> TYPE: PRT
<213> ORGANISM: Artificial Sequence
<220> FEATURE:
<223> OTHER INFORMATION: Synthetic phosphopeptide manufactured by
      trypsin digestion of the artificial precursor-peptide
<220> FEATURE:
<221> NAME/KEY: misc_feature
<222> LOCATION: (9)..(9)
<223> OTHER INFORMATION: phosphorylated tyrosine

<400> SEQUENCE: 2

```
Gly Ser Thr Ala Glu Asn Ala Glu Tyr Leu Arg
1               5                   10
```

<210> SEQ ID NO 3
<211> LENGTH: 22
<212> TYPE: PRT
<213> ORGANISM: Artificial Sequence
<220> FEATURE:
<223> OTHER INFORMATION: Synthetic precursor-peptide
<220> FEATURE:
<221> NAME/KEY: misc_feature
<222> LOCATION: (9)..(9)
<223> OTHER INFORMATION: phosphorylated tyrosine

<400> SEQUENCE: 3

```
Gly Ser Thr Ala Glu Asn Ala Glu Tyr Leu Arg Gly Ser Thr Ala Glu
1               5                   10                  15

Asn Ala Glu Tyr Leu Arg
            20
```

<210> SEQ ID NO 4
<211> LENGTH: 11
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 4

```
Gly Ser Thr Ala Glu Asn Ala Glu Tyr Leu Arg
1               5                   10
```

<210> SEQ ID NO 5
<211> LENGTH: 11
<212> TYPE: PRT
<213> ORGANISM: Artificial Sequence
<220> FEATURE:
<223> OTHER INFORMATION: Synthetic phosphopeptide manufactured by
      trypsin digestion of the artificial precursor-peptide
<220> FEATURE:
<221> NAME/KEY: misc_feature
<222> LOCATION: (9)..(9)
<223> OTHER INFORMATION: phosphorylated tyrosine

<400> SEQUENCE: 5

```
Gly Ser Thr Ala Glu Asn Ala Glu Tyr Leu Arg
1               5                   10
```

<210> SEQ ID NO 6
<211> LENGTH: 18
<212> TYPE: PRT
<213> ORGANISM: Artificial Sequence
<220> FEATURE:
<223> OTHER INFORMATION: Synthetic artificial precursor-peptide

```
<400> SEQUENCE: 6

His Tyr Gln Pro Tyr Ala Pro Pro Arg His Tyr Gln Pro Tyr Ala Pro
1               5                   10                  15

Pro Ala

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 7

His Tyr Gln Pro Tyr Ala Pro Pro Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 8

His Tyr Gln Pro Tyr Ala Pro Pro Ala
1               5

<210> SEQ ID NO 9
<211> LENGTH: 34
<212> TYPE: PRT
<213> ORGANISM: Artificial Sequence
<220> FEATURE:
<223> OTHER INFORMATION: Synthetic artificial precursor-peptide

<400> SEQUENCE: 9

Asp Ser Ala Thr Pro Glu Ala Leu Ala Phe Val Asp Ser Ala Thr Pro
1               5                   10                  15

Glu Ala Leu Ala Phe Val Asp Ser Ala Thr Pro Glu Ala Leu Ala Phe
            20                  25                  30

Val Arg

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 10

Asp Ser Ala Thr Pro Glu Ala Leu Ala Phe Val
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 11

Asp Ser Ala Thr Pro Glu Ala Leu Ala Phe Arg
1               5                   10
```

```
<210> SEQ ID NO 12
<211> LENGTH: 11
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 12

Gly Ser Thr Ala Glu Asn Ala Glu Tyr Leu Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic phosphopeptide manufactured by
      trypsin digestion of the artificial precursor-peptide
<220> FEATURE:
<221> NAME/KEY: misc_feature
<222> LOCATION: (9)..(9)
<223> OTHER INFORMATION: phosphorylated tyrosine

<400> SEQUENCE: 13

Gly Ser Thr Ala Glu Asn Ala Glu Tyr Leu Arg
1               5                   10

<210> SEQ ID NO 14
<211> LENGTH: 22
<212> TYPE: PRT
<213> ORGANISM: Artificial Sequence
<220> FEATURE:
<223> OTHER INFORMATION: Synthetic artificial precursor-peptide
<220> FEATURE:
<221> NAME/KEY: misc_feature
<222> LOCATION: (9)..(9)
<223> OTHER INFORMATION: phosphorylated tyrosine

<400> SEQUENCE: 14

Gly Ser Thr Ala Glu Asn Ala Glu Tyr Leu Arg Gly Ser Thr Ala Glu
1               5                   10                  15

Asn Ala Glu Tyr Leu Arg
            20

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 15

Gly Ser Thr Ala Glu Asn Ala Glu Tyr Leu Arg
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Synthetic phosphopeptide manufactured by
      trypsin digestion of the artificial precursor-peptide
<220> FEATURE:
<221> NAME/KEY: misc_feature
<222> LOCATION: (9)..(9)
<223> OTHER INFORMATION: phosphorylated tyrosine
```

-continued

```
<400> SEQUENCE: 16

Gly Ser Thr Ala Glu Asn Ala Glu Tyr Leu Arg
1               5                   10

<210> SEQ ID NO 17
<211> LENGTH: 18
<212> TYPE: PRT
<213> ORGANISM: Artificial Sequence
<220> FEATURE:
<223> OTHER INFORMATION: Synthetic artificial precursor-peptide
<220> FEATURE:
<221> NAME/KEY: misc_feature
<222> LOCATION: (5)..(5)
<223> OTHER INFORMATION: phosphorylated tyrosine

<400> SEQUENCE: 17

His Tyr Gln Pro Tyr Ala Pro Pro Arg His Tyr Gln Pro Tyr Ala Pro
1               5                   10                  15

Pro Arg

<210> SEQ ID NO 18
<211> LENGTH: 9
<212> TYPE: PRT
<213> ORGANISM: Artificial Sequence
<220> FEATURE:
<223> OTHER INFORMATION: Synthetic phosphopeptide manufactured by
      trypsin digestion of the artificial precursor-peptide
<220> FEATURE:
<221> NAME/KEY: misc_feature
<222> LOCATION: (5)..(5)
<223> OTHER INFORMATION: phosphorylated tyrosine

<400> SEQUENCE: 18

His Tyr Gln Pro Tyr Ala Pro Pro Arg
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide manufactured by trypsin
      digestion of the artificial precursor-peptide

<400> SEQUENCE: 19

His Tyr Gln Pro Tyr Ala Pro Pro Arg
1               5
```

METHOD FOR DETERMINING THE RATIO OF TWO DISTINCT PEPTIDES OR POLYNUCLEIC ACIDS

BACKGROUND OF THE INVENTION

The present invention relates generally to the fields of analytics of proteins, peptides, DNA and RNA. More particularly, the invention concerns determination of the exact ratio of protein, peptide, DNA or RNA isoforms in a sample. More specially, the invention relates to the use of a defined precursor to measure the relative amounts of closely related protein, peptide, DNA or RNA isoforms such as phosphoisoforms from a synthetic or biological sample.

With the completion of the Human Genome Project, the emphasis is shifting to examining the protein complement in the human organism. This has given a rise to the science of proteomics, the study of the whole amount of the proteins produced by a cell type of an organism. At the same time, there has been a revival of interest in proteomics in many prokaryotes and lower eukaryotes as well.

The term proteome refers to all the different proteins expressed by a genome and thus involves the identification of proteins in the body and the detection of their physiological and pathophysiological function. The about 30.000 genes, defined by the Human Genome project translate into 30.000 up to 1 million of proteins, when alternate splicing and post-translational modifications are considered. While a specific genome remains unchanged to a high extent, the proteins in any particular cell change dramatically as genes are turned on and off in response to extracellular stimulation.

As a reflection of the dynamic nature of the proteome, the term "functional proteome" is preferred by some scientists, which describes the whole amount of proteins produced by a single cell in a single time frame. Finally, it is believed, that through proteomics, new disease markers and drug targets can be identified that will help design new products to prevent, diagnose and treat disease.

One of the most common protein modifications is phosphorylation. It is estimated, that about 30% of all proteins in mammalian cells are phosphorylated at any given time and that about 5% of the vertebrate genome encodes protein kinases and phosphatases, underlining the importance of this protein modification. The presence of various protein kinases and phosphatases permits the use of quickly reversible phosphorylation in a vast number of different, highly regulated pathways and functions, including signal transduction, cell division, apoptosis regulation, and cell differentiation.

Knowledge of the phosphorylation site is crucial for detailed understanding various different regulatory processes in cells. This knowledge requires sensitive and highly sophisticated analysis methods. Theoretically, the most sensitive method for detecting of phosphorylation is to incorporate radioactive phosphorus isotopes before phosphopeptide mapping and/or Edman degradation. However, e.g. in tissue samples, the incorporation of radioactive isotopes is not possible or is very inefficient in the cause of cell culture due to the presence of unlabeled ATP. Moreover, high levels of radioactive derivatives, incorporated in the cell may cause cellular damage and can thereby alter phosphorylation.

Protein phosphorylation analysis by mass spectrometry has a structural and two quantitative aspects. The structural aspect refers to the identification of the phosphorylated site (recognition of phosphorylated amino acid residue and its position within the protein chain). The quantitative aspects comprise the determination of the phosphorylation degree (equivalent term: phosphorylation stoichiometry), which is the molar ratio between the phosphorylated and unphosphorylated residue at a particular position in the protein chain (relative quantification), and the determination of the amount of phosphoprotein (or phosphopeptide) present, which carries a particular phosphorylation site (absolute quantification). Considering the fact, that protein phosphorylation analysis is of major interest in many laboratories around the world, it is surprising, that more information about protein phosphorylation sites and about the ratio of phosphorylation of these sites has not been gathered since the discovery of protein phosphorylation. One reason is the generally low phosphorylation stoichiometry of most proteins such that phosphopeptides are widely underrepresented in the generated protein or peptide mixtures.

As the issue of phosphorylation stoichiometry is less commonly addressed, several publications deal with the problem of determining the ratio of two different targets, in particular the ratio of two different target-peptides.

US 2004/0119010 A1 discloses a method for quantifying the amounts of proteins and peptides, including those that are closely related isoforms, using matrix-assisted laser desorption/ionization time of flight mass spectrometry (MALDI-TOF-MS). According to this laid open publication, a method of quantitatively comparing the amount of a plurality of structurally distinct proteins, or peptides is disclosed. This method comprises the steps of obtaining one or more samples containing said multiply distinct target proteins or peptides, providing a standard, wherein the standard is a derivative of the target protein or peptide of interest at a known or measurable quantity, co-crystallizing the target proteins or the standard with a matrix, analyzing the crystallized target proteins or peptides and standard using matrix-assisted laser desorption/ionization time of flight (MALDI-TOF) mass spectrometry; and determining relative and absolute protein or peptide analyzed, that is present in the sample. According to the teaching of this document, the standards are proteins or peptides derived or synthesized directly from the proteins of interest, what implicates imprecisions in the exact quantity of the used standards.

A further problem, which has to be mentioned, is the so called response, also called flyability in mass spectrometry of phosphoproteins. H. Steen et al., teaches in: *stable isotope-free relative and absolute quantitation of protein phosphorylation stoichiometry by MS*, Steen H., PNAS, 11, 2005, that determination of the stoichiometry of phosphoproteins would be an easy task, if peptides and their phosphorylated cognates had identical ionization/detection efficiencies because it would be sufficient to monitor the peptide and the phosphorylated complement and calculate the intensity ratio between these two species. In this publication, H. Steen suggests to determine the flyability for at least two samples of a peptide/phosphopeptide pair. These two samples must be interconnected by a treatment resulting in partial dephosphorylation (e.g. induced by phosphatase), so that the changes in the phosphorylation degree between these two samples are interconnected in the following way: the decrease in the amount of phosphopeptide in the treated sample is equivalent to the increase of the nonphosphorylated cognate in that sample. To test this approach, several synthetic peptides and their phosphorylated cognates were purified to homogeneity and quantified by amino acid analysis. These synthetic standards are mixed in varying but defined ratios and analyzed in replicate by LC/MS. Afterwards, the flyability ratios for these synthetic peptide pairs were calculated by using the defined mixture ratio and measured ion currents. The use of synthetic standards, quantified according to the state of the art, still includes the aberrations of the method used in the quantification of the standards and bears significant deviations in the determination in the flyability.

Summing up the above, there remains a need for improvements in methods for determining the exact ratio of distinct target-proteins, -peptides, -DNA or RNA. However these methods imply purchasing a standard with an exact ratio of standard proteins, peptides, RNA or DNA. No standards with these properties are currently available.

SUMMARY OF THE INVENTION

Thus, in accordance with the present invention, there is provided a method for determining the ratio of two distinct target-peptides or -polynucleic acids comprising the steps:
(a) obtaining a sample containing said two distinct target-peptides or -polynucleic acids,
(b) providing a precursor-peptide or -polynucleic acid, comprising the two distinct target-peptides or -polynucleic acids in a known ratio, wherein the two distinct target-peptides or -polynucleic acids are connected by a cleavage site,
(c) cleaving the precursor-peptides or -polynucleic acids at the cleavage site to obtain a standard with the known ratio of the two distinct target-peptides or -polynucleic acids,
(d) detecting a signal of the distinct target-peptides or -polynucleic acids of the standard in an analyzer, comparing the signals with the known ratio and determining a correction factor,
(e) detecting the signal of the distinct target-peptides or -polynucleic acids of the sample in the analyzer and
(f) determining the ratio of the two distinct target-peptides or -polynucleic acids by means of the correction factor.

The term "peptide" used in the present invention can also encompass conjugated or unconjugated proteins.

According to the present invention, the term "target peptide" concerns both, the target peptides or peptides of interest, that are present in the sample and the two distinct other forms of said peptides that are present in the precursor peptide. Cleaving of the precursor peptide leads to the two distinct target peptides with known ratio.

The term "polynucleic acids" comprises DNA and RNA strands and parts thereof.

In one embodiment of the invention, the distinct target-peptides are isoforms of a peptide, and according to a preferred embodiment of the invention, these isoforms are phosphoisoforms of the target-peptide.

Apart from the examples mentioned above, the isoforms of said peptides can differ from their degree of glycosylation and/or acetylation and/or alkylation and/or tyrosine sulfatation and/or biotinylation and/or isoprenylation and/or ubiquitination and/or glutamylation and/or oxidation and/or racemisation and/or isomerisation.

In the case of determining the ratio of two distinct target DNA strands, the DNA strands are preferably isoforms from the same DNA strand with a different rate of methylation.

In a particular embodiment of the invention, the sample containing said two targets may be derived from a cell, a prokaryotic cell, a eukaryotic cell, a mammalian cell or a human cell. The sample may also be derived from an organ or a human organ. The sample containing said two distinct targets may further be derived from plasma or from serum.

According to a preferred embodiment of the invention, the peptides of the sample may be produced by proteolytic cleavage of a target protein. They may also be produced by chemical cleavage or enzymatic digestion of said protein. In a further preferred embodiment of the invention, said enzymatic cleavage can be performed by an endopeptidase, a protease, or any proteolytic digestive enzyme.

According to a further aspect of the invention, the samples are pre-purified, for example using a separation device, for example a HPLC. Further in the case of analysis of phosphoproteins, selective phosphopeptide enrichment methods can be conducted. This selective enrichment of phosphoproteins can involve the usage of metal chelate affinity prior to digestion or phosphospecific antibody enrichment of phosphoproteins, such as those phosphorylated on tyrosine residues. Affinity purification of phosphopeptides from proteolytic digests can be performed by immunoaffinity methods, metal chelate affinity chromatography, ion exchange fractionation or a combination thereof prior to reverse phase LC-MS.

According to the invention, a precursor-peptide or -polynucleic acid comprising the two distinct target-peptides or -polynucleic acids in a known ratio is provided. Preferably, the precursor comprises the two targets in a 1:3 ratio, more preferred in a 1:2 ratio, most preferred in a 1:1 ratio. According to the invention, the two target-peptides or -polynucleic acids are connected by a cleavage site.

Appropriate cleavage sites depend on the proteases used in the digest of the precursor. The proteases differ in their substrate specificity. For example, chymotrypsin prefers an aromatic side chain on the residue whose carbonyl carbon is part of the peptide bond to be cleaved. Trypsin prefers a positively charged Lys or Arg residue at this position. Caspases get their name from the fact that they cleave on the carboxyl side of an aspartate residue. The choice of the enzyme used in the digestion depends on the sequence of the targets.

The synthesis of the precursor-peptide or the precursor-polynucleotide of the invention can be synthesized by any method known in the art. As an example solid phase peptide synthesis is mentioned.

The precursor is cleaved at the cleavage site to obtain a standard with a known ratio of the two distinct target-peptides or -polynucleic acids. By cleavage of the precursor, a standard comprising the two peptides or polynucleic acids in the exact ratio is obtained.

According to the invention, the precursor is provided to obtain a standard comprising two peptides or polynucleic acids of interest after cleavage of the precursor. Because the two peptides or polynucleic acids derive from the precursor, there is no variance in the ratio of said two peptides or polynucleic acids in the standard. Hence, the present method is free from deviations, which derive from weighting or the quantification of the polypeptides or polynucleic acids. It is apparent from the present invention that every single cleavage of the precursor results in exactly two fragments of the precursor.

The inventor found out, that by determining the signal ratio for a particular pair of distinct peptides or polynucleic acids and comparing this signal ratio with the known ratio of the standard, the standard ratio can be used to correct the signal of the corresponding distinct species and to calculate the relative stoichiometry of the distinct isoforms of a sample.

In a particular embodiment of the invention, the standard peptides may be produced by proteolytic cleavage of the precursor. It may also be produced by chemical cleavage or enzymatic digestion of the precursor. Enzymatic digestions are more common. An ideal digestion cuts only at a specific amino acid, but cuts all occurrences of that amino acid. In a further preferred embodiment of the invention, said enzymatic cleavage can be performed by an endopeptidase, a protease, any proteolytic digestive enzyme in the case of proteins or peptides. In the case of DNA or RNA, any DNase or RNase or any restriction enzyme can be used to cleave the precursor at the cleavage site between the target strands.

In the case, that the precursor comprises two or more polynucleic acid strands, the polynucleic strands are connected by a palindromic or partially palindromic site. The palindrome is defined as dyad symmetry around one axis and is the cleavage site for the nucleases.

The cleavage site of the precursor may be part of the distinct peptides or polynucleic acids. According to a further aspect, the cleavage site may lie on a spacer sequence between the two distinct targets. In that case, the spacer sequence is preferably divisible into two parts of identical masses, when mass spectrometry is used.

According to a further embodiment of the invention, it was found that it is advantageous to purify the precursor prior the cleavage to avoid unintentional impurities in the standard, which could falsify or hamper the intensity ratio measurement. The purification can be carried out using standard separation methods, such as chromatographic or electrophoretic separation methods.

Selection of the reference peptides or polynucleic acids (standard) for the precursor is an important aspect of accurate determination of their ratio. For a given protein, a signature peptide or peptides have to be selected, that bears e.g. the phosphorylation site of interest. Advantageously, the selected peptide comprises 3 to 15 amino acids, more preferred, 6 to 12 amino acids, most preferred 10 amino acids. After selection of the peptide, a precursor has to be synthesized that comprises the two isoforms of the selected peptide, which are connected by a selected cleavage site to allow a specific enzyme to cleave the precursor into two parts.

The cleavage of the precursor leads to a standard, comprising at least three different strands, strains or chains, respectively. A certain amount of undigested precursor and further a certain amount of the two distinct target-peptides or -polynucleic acids in an exact ratio. The precursor can be prepared in any suitable manner. For example, the precursors may be prepared biologically using cell cultures of naturally-occurring or recombinant cell types; or may be prepared synthetically by a chemical synthesis.

In another embodiment of the invention, when a precursor with a 1:2 or 1:3 ratio is used, a control, that the digest has been carried out quantitatively and no uncleaved or not completely cleaved precursor-polymers are present in the standard, is necessary. Such a control can be conducted using conventional mass spectrometric analysis.

According to the invention, the signal of each distinct target-peptide or -nucleic acid of the standard with a known ratio of the distinct targets is detected in an analyzer. The relative ratio of the target-peptides or -polynucleic acids is identified and the correction factor is determined. Because the ratio of—for example—a particular peptide/phosphopeptide pair is exactly 1:1 or 1:2 or 1:3, this ratio can be used to determine the exact response to correct the signals of a corresponding species, to determine the phosphorylation stoichiometry in a sample of an unknown phosphorylation stoichiometry, using the correction factor, or performing a double ratio determination (ratio peptide/peptide standard over ratio isoform-peptide/isoform-peptide standard) eliminating the necessity for correction factor determination.

According to the invention, the number of phosphorylation sites of the target peptide ranges from 1 to 3. According to this, the precursor-peptide comprises two distinct peptides, which differ in one phosphorylated amino acid. According to a further embodiment of the invention, the precursor-peptide may comprise at least two distinct peptides, which differ in two or three phosphorylated amino acids.

Further, the signal of the distinct target-peptides or -polynucleic acids of the sample is detected in the same analyzer using identical conditions and instrumental parameter settings. Afterwards the exact ratio of the two distinct target-peptides or -polynucleic acids is determined, using the correction factor.

The term "peptide" includes any molecule comprising two or more amino acids joined to each other by, e.g. amide bonds. The term refers both to short chains (e.g. oligopeptides with fewer than 20 amino acids) and to longer chains (e.g. polypeptides with 20 or more amino acids). The term "peptide" used herein can also encompass whole proteins. The peptide may be a linear, cyclic or branched peptide or derivatives thereof like isosteres.

According to the invention the precursor-peptide or precursor-polynucleic acid comprises distinct target proteins or polynucleic acids with a size of 3 to 15 subunits, more preferred with a size of 6 to 12 subunits, most preferred with a size of 10 subunits, wherein the subunit is an amino acid or a nucleotide or an derivative of the aforementioned.

According to a further embodiment of the invention the precursor-peptide is cleaved by enzymatic digestion. Suitable enzymatic agents for peptides include, but are not limited to Trypsin, Arg-C, Asp-N, chymotrypsin, Lys-C, Lys-C/P, Pepsin, Pancreatic Elastase, Thermolysin, Clostripain, V8-DE, V8-E, Thrombin, Factor Xa Protease, Enterokinase, Enteropeptidase. Suitable enzymatic agents for DNA include, but are not limited to Ava I, Bam H1, Bgl II, Eco R1, Eco R2, Hae I, Hha I, Hind III, Mbo I, Sma I, Taq I, Xma I.

Preferably, the precursor-peptide is cleaved by a non-enzymatic chemical cleavage. Suitable non-enzymatic cleavage reagents for peptides include, but are not limited to, CNBr, formic acid, hydroxylamine, etc.

Consequently, enzymes that cleave at very rare positions are preferred in the present invention to avoid an unintentional degradation of the precursor-peptide or -polynucleotide acid.

In a preferred embodiment of the invention, using a mass spectrometer as analyzer, a stable isotope labeled precursor is provided. The inventor has further found that a protein, peptide, DNA or RNA can be furnished using stable isotopes for example of carbon, nitrogen, sulphur, oxygen, and hydrogen, such as $^2H$, $^{13}C$, $^{15}N$, $^{18}O$ or $^{34}S$. The incorporation of a specific amount of stable isotopes, for example by labelling of a specific amino acid or base, results in a defined mass-shift hence, the use of a stable isotope marked precursor enables to apply the precursor to the sample subsequent to step (c) and to cleave and/or digest the standard and the sample simultaneously. According to this, the stable isotope marked precursor is added to the sample and the digestion and analysis is processed simultaneously. According to this preferred embodiment of the invention, the ratio of the two distinct target-peptides or -polynucleic acids is determined by double ratio calculation (calculation of the ratio of two intensity ratios—namely of the peptide and isoform-peptide with their corresponding labeled standards) to eliminate the compound-specific correction factors.

The ratio of phosphorylation can be calculated using the following formulae 1 to 5:

$$\text{intensity ratio (peptide)} = \frac{c(pep_m) \times \text{factor}(pep_m)}{c(pep) \times \text{factor}(pep)} \quad \text{Formula 1}$$

$$\text{intensity ratio (P-peptide)} = \frac{c(P\text{-}pep_m) \times \text{factor}(P\text{-}pep_m)}{c(P\text{-}pep) \times \text{factor}(P\text{-}pep)} \quad \text{Formula 2}$$

$$\frac{\text{intensity ratio } (pep)}{\text{intensity ratio } (P\text{-}pep)} = \frac{c(pep_m)}{c(pep)} \times \frac{c(P\text{-}pep)}{c(P\text{-}pep_m)} \quad \text{Formula 3}$$

$$\frac{\text{intensity ratio } (pep)}{\text{intensity ratio } (P\text{-}pep)} = \quad \text{Formula 4}$$

$$\frac{c(P\text{-}pep)}{c(pep)} = \text{molar ratio } (P\text{-}pep/pep)$$

Phosphorylation Degree [%] = \quad Formula 5

$$\frac{\text{molar ratio } (P\text{-}pep/pep)}{1 + \text{molar ratio } (P\text{-}pep/pep)} \times 100$$

Wherein: c(pep) is the concentration of the peptide; c(P-pep) is the concentration of the phosphopeptide; $c(pep_m)$ is the concentration of the labeled peptide; $c(P\text{-}pep_m)$ is the concentration of the labeled phosphopeptide, concentrations are preferably given in mol/l.

According to the invention, the concentrations of $c(pep_m)$ [mol/l] and ($c(P\text{-}pep_m)$) [mol/l] are equal.

The experimentally determined phosphorylation ratio is more accurate, the closer the experimentally determined intensity ratio is to 1.

The inventive method for determining the ratio of two distinct target-peptides or polynucleic acids can be performed using a variety of different analyzers.

According to the invention, the analyzer used in the inventive method, is a mass spectrometer. Suitable mass spectrometers or mass analyzers include, but are not limited to, time of flight (TOF), quadrupole time of flight (Q-TOF), ion trap (IT), quadrupole ion trap (Q-IT), triple quadrupole (QQQ), Fourier transform mass spectrometry (FTMS), and Fourier transfer ion cyclotron resonance (FTICR) mass analyzers. Preferably, the mass analyzer is a TOF mass analyzer. More preferred the mass analyzer is a Q-TOF mass spectrometer or a MALDI-Q-TOF mass spectrometer to determine the signals of the target- and standard-components.

The inventor has found that it is advantageous when the mass spectrometer further comprises an upstream chromatograph. Suitable chromatographs include, but are not limited to, high performance liquid chromatography (HPLC), fast-centrifugal-partition-Chromatography (FCPC), optimum-performance-laminar-chromatography (OPLC).

The inventive method is not restricted in using mass spectrometers as mentioned above. Moreover, each chromatographic device that has the ability to separate the targets and standard and provides a signal of the targets and the standard is suitable for the method according to the invention.

The inventor has also found, that a peptide or polynucleic acid can be analyzed according to the inventive method, using intrinsic fluorescence or fluorescence labels, such as fluorescent dyes. In this case, it is necessary that the analyzer is a fluorescence-analyzer such as a fluorescence-spectrometer.

According to a further aspect of the invention, the inventor found out, that it is possible, to use a detection device for radioactivity, when the distinct target-peptides are labeled with radioactive nuclides. In this case, suitable analyzers include, but are not limited to, scintillation detectors und counters.

The following figures and examples are included to further illustrate various aspects of the present invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and the scope of the invention.

EXAMPLES

Example 1

Figure 1:
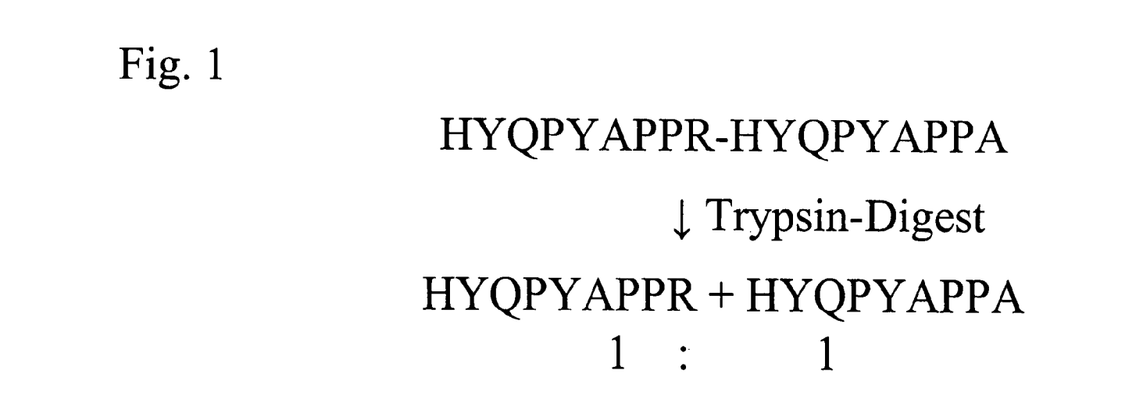
FIG. 1 shows an exemplary embodiment of an amino acid sequence of a precursor-peptide, which consists of 2 peptide subunits. (SEQ ID NOS: 6, 7, and 8)

In FIG. 1, an exemplary precursor-peptide is shown. The exemplary precursor-peptide consists of 18 amino acids and contains a cleavage site for the serine endopeptidase trypsin between the amino acids arginine and histidine. The proteolytic cleavage of the precursor-peptide between arginine and histidine results in an exact 1:1 mixture of two 9-amino acid-peptides, wherein the two peptides differ from their terminal amino acid.

The precursor shown in FIG. 1 is suitable for manufacturing of a standard that is applicable to determine the exact ratio of two peptides with corresponding amino acid sequences of unknown ratio in a sample.

Example 2

Figure 2:
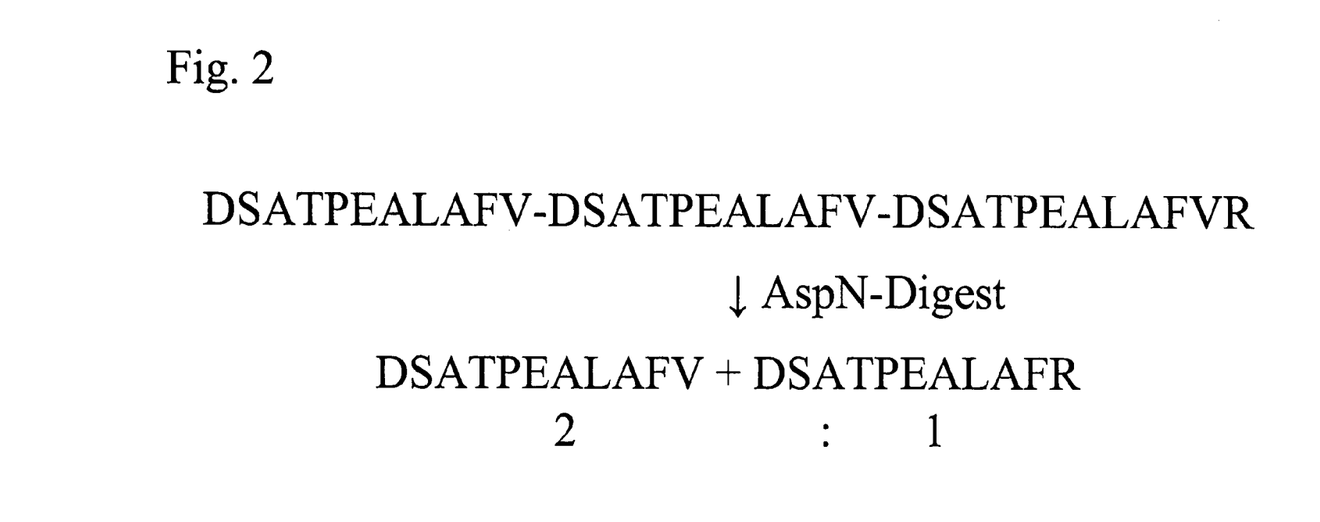
FIG. 2 shows an exemplary embodiment of an amino acid sequence of a precursor-peptide, which consists of 3 peptide-subunits. (SEQ ID NOS: 9, 10 and 11)

FIG. 2 shows an exemplary precursor-peptide that consists of 33 amino acids and is cleavable by the protease AspN into two different 11 amino acid peptides in a stoichiometric ratio of 1:2.

Precursor peptides of the type as shown in FIG. 2 are suitable for the determination of the ratio of two different peptides, wherein the signal of one of the two different peptides is considerably minor. In that case, a precursor is provided, that comprises the peptides in a stoichiometric ratio of 1:2 or 1:3, whereby the precursor comprises 2 or 3 of the peptides with the major signal.

Example 3

Figure 3:
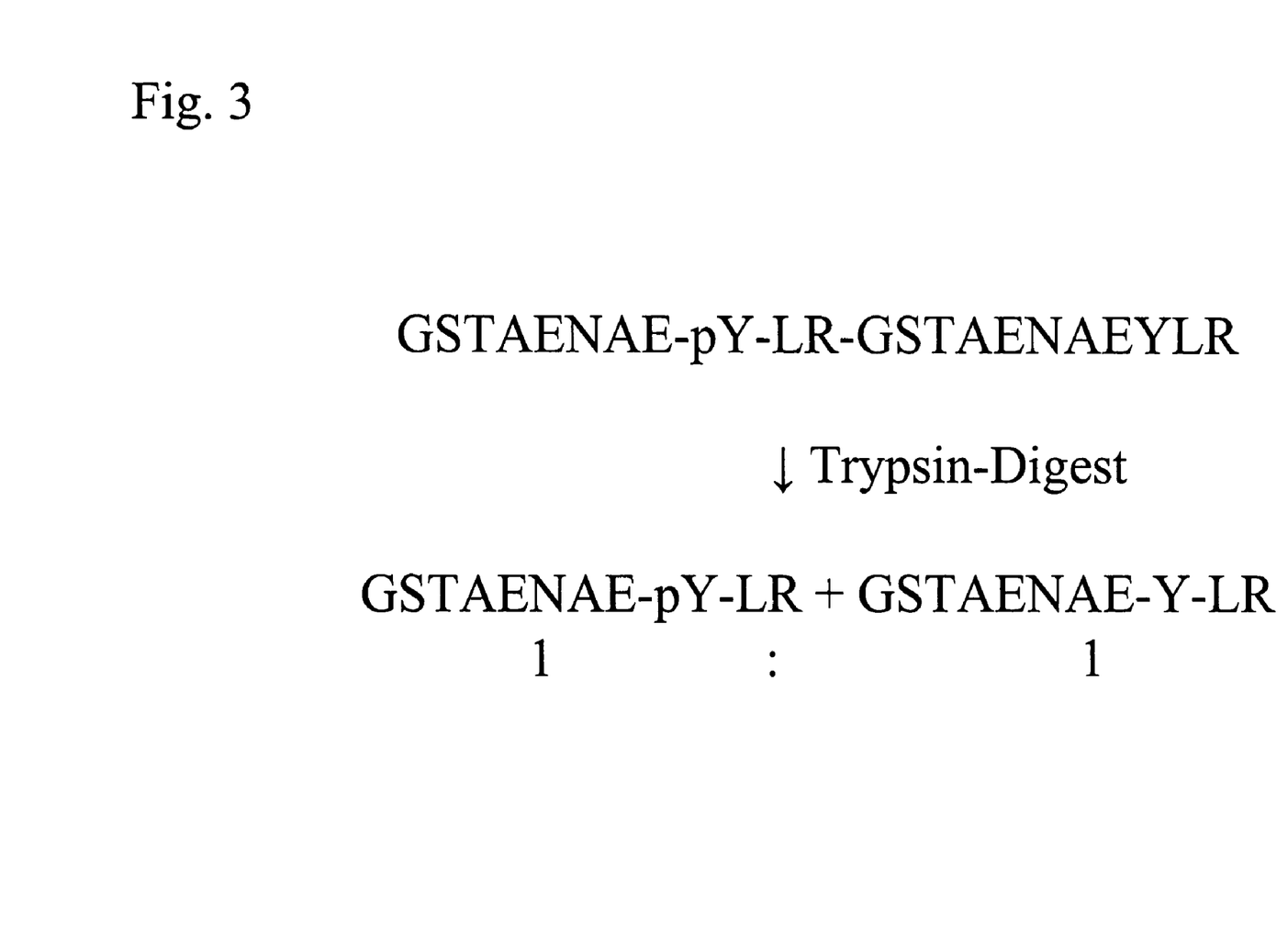
FIG. 3 shows an exemplary embodiment of an amino acid sequence of a precursor-peptide, which comprises a phosphorylated peptide. (SEQ ID NOS: 14, 13, and 12)

The exemplary embodiment of an amino acid sequence of a precursor-peptide, which comprises a phosphorylated peptide, is shown in FIG. 3. The precursor-peptide comprises the phosphorylated amino acid tyrosine. The proteolytic cleavage of said precursor-peptide, using the serine protease trypsin, leads to a 1:1 standard, comprising the phosphorylated precursor-peptide, a phosphorylated peptide and an unphosphorylated peptide. The results of the mass spectrometry analysis of this sample are shown in FIG. 4.

Example 4

Figure 4:
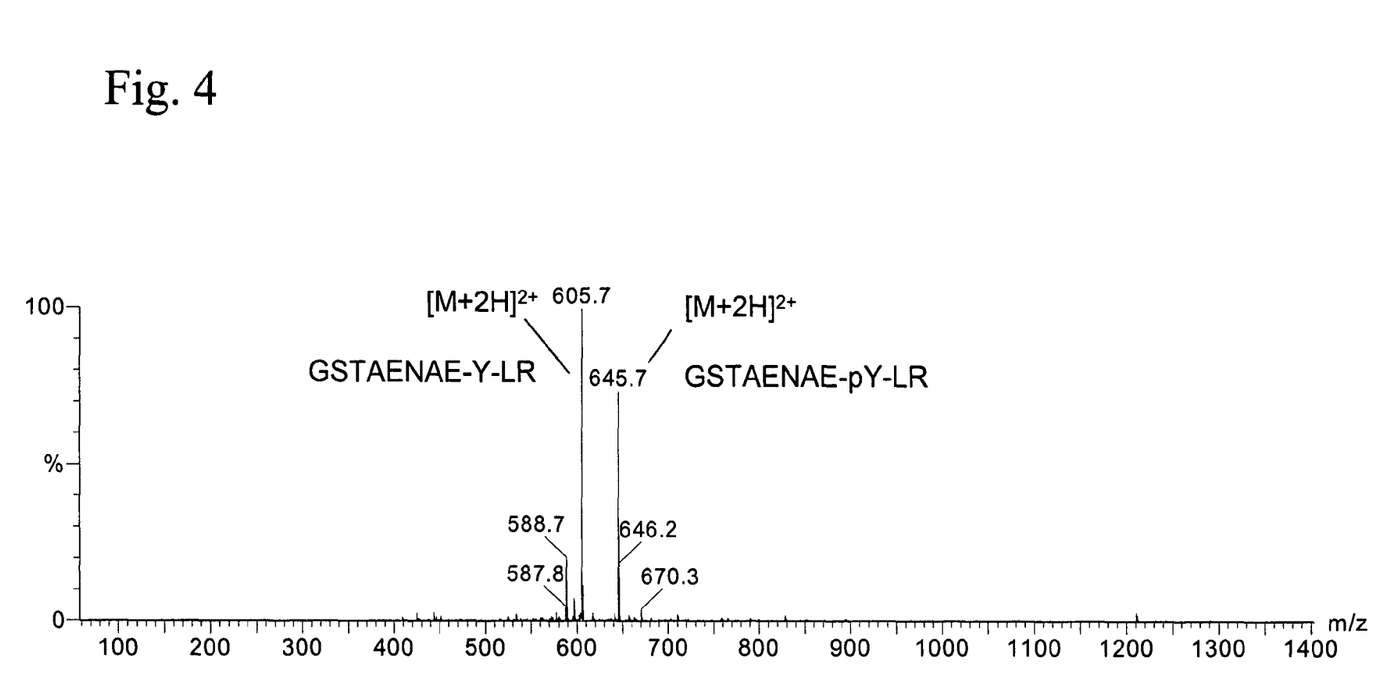
FIG. 4 shows the ESI-TOF-MS spectrum of the cleaved precursor-peptide of example in FIG. 3. (SEQ ID NOS: 15 and 16)

FIG. 4 shows the ESI-Q-TOF-MS spectrum of the cleaved precursor-peptide of example 3. The precursor-peptide of example 3 is digested by trypsin, into two peptides in an exact 1:1 ratio and analyzed in an ESI-Q-TOF-MS. From the signal intensities of the phosphorylated and the unphosphorylated peptides, it is clearly visible, that peptides and their phosphorylated counterparts can have significantly different flyabilities. In the exact 1:1 molar mixture of the peptide GSTAE-NAE-Y-LR (SEQ ID NO: 1) and the phosphopeptide GSTAENAE-pY-LR (SEQ ID NO: 2), which was manufactured by trypsin digestion of the precursor-peptide GSTAE-NAE-pY-LRGSTAENAEYLR (SEQ ID NO: 3) the signal of the peptide is significantly more intensive than the signal of the phosphopeptide. Hence, the detection efficiency of the phosphopeptide compared to its unmodified cognate is significantly lower. This notion is based on the idea that the phosphate group of phosphorylated species is negatively charged, thereby affecting the ionization and detection efficiencies under acidic conditions used for mass spectrometric experiments in positive ion mode.

The present invention discloses a method for determining the ratio of two distinct target-peptides using the standard with an exact ratio of a phosphorylated peptide and its unphosphorylated cognate for the calibration of the analyzer. After this calibration, the relative amount of a phosphopeptide and its unphosphorylated cognate in a sample, whereby the two peptides are identical to those used for the calibration, can be analyzed using the same analyzer.

Example 5

Figure 5:
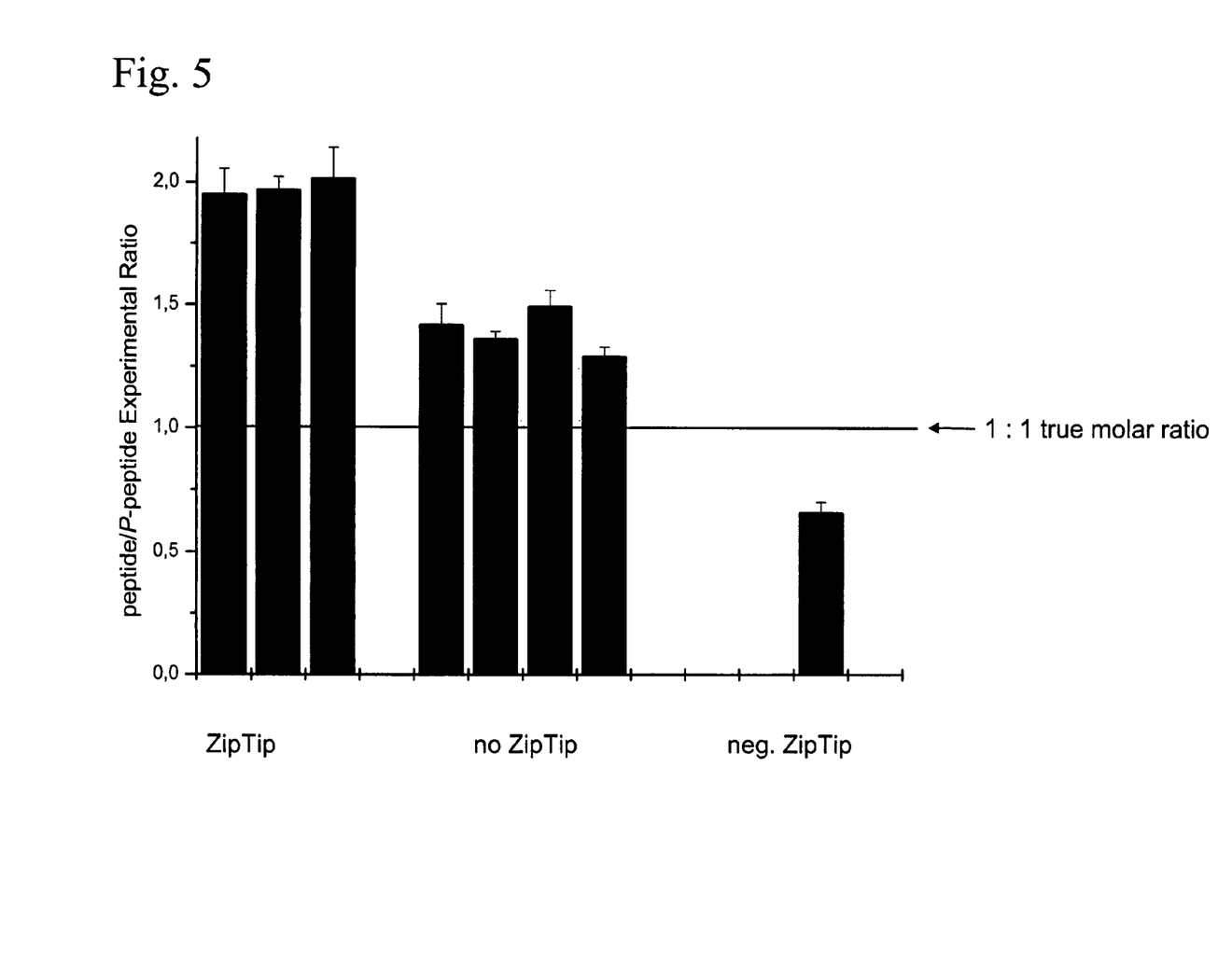
FIG. 5 shows the experimental intensity ratios of a 1:1 molar mixture of a peptide/phosphopeptide analyzed in positive ion mode; middle part: without desalting, positive ion mode; left part: after desalting, positive ion mode; right part (single column), without desalting, negative ion mode.

FIG. 5 shows the analysis of an exactly equimolar mixture of the two peptides GSTAENAE-Y-LR (SEQ ID NO: 4) and GSTAENAE-pY-LR (SEQ ID NO: 5). This mixture was prepared from a precursor peptide by trypsin cleavage as outlined before. Central part (4 measurements, positive ion mode): the mixture was analyzed directly after trypsin cleavage without further treatment. The signal ratio peptide/phosphopeptide of about 1.4 reflects the difference in ionization efficiency (flyability) between the two peptides, which is lower for the phosphopeptide; Left part (3 measurements, positive ion mode): same analysis after desalting of the sample by a ZipTip C18 microcolumn (desalting is a common step during sample preparation for ESI-MS), the higher ratio of about two reflects a lower recovery the phosphopeptide in the desalted sample, which is in agreement with general experimental observations; Right part (1 experiment, negative ion mode): the original mixture was analyzed and a preferential ionization of the phosphopeptide is observed, which is in agreement with general experience, which shows increased ionization efficiency (flyability) of phosphopeptides versus cognate peptides in negative ion mode.

Example 6

Figure 6:
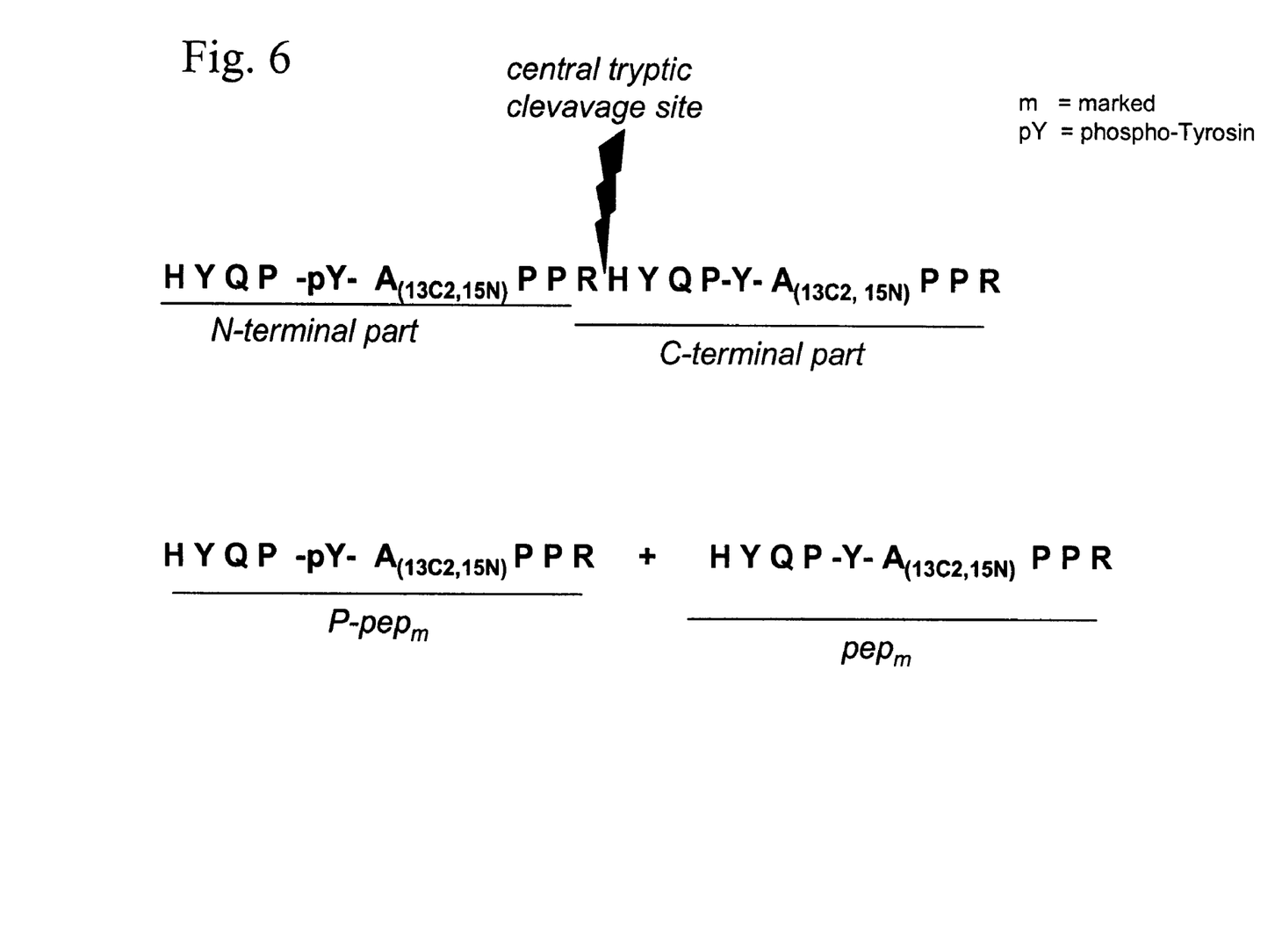
FIG. 6 shows an exemplary embodiment of a precursor-peptide, labeled with stable isotopes $^{13}C$ and $^{15}N$. (SEQ ID NOS: 17, 18, and 19)

FIG. 6 shows an exemplary embodiment of a precursor-peptide, wherein the amino acid alanine is incorporated, that is marked with stable isotopes $^{13}C$ and $^{15}N$. Hence, a stable isotope marked precursor is provided, that is furnished with a stable isotope. At its N-terminus, the phosphopeptide compound of the precursor comprises the amino acid alanine, which is marked with two stabile radioisotopes $^{13}C$ and one $^{15}N$ isotope. At its C-terminal end, the precursor-peptide comprises a stable isotope marked peptide that comprises the amino acid alanine, which is marked with two stable isotopes $^{13}C$ and one $^{15}N$ isotope, too. This labeling with stable isotopes leads to a mass shift of 3 Dalton, compared to the corresponding unlabeled peptides of the same sequence.

One disadvantage of mass spectrometry is that the signal will vary between runs due to differences in sample introduction, ionization process, ion acceleration, ion separation, and ion detection. Therefore any type of MS quantification will rely on internal standards that undergo the same process as the analyte.

A trypsin digest of the precursor-peptide leads to a labeled peptide and a labeled phosphopeptide that differ from their unlabeled cognates in a mass difference of 3 Dalton. According to this, it is possible to apply the stable isotope marked precursor as an internal standard to the sample and to conduct the digestion and analysis of the precursor peptide and the sample simultaneously.

Example 7

Figure 7:
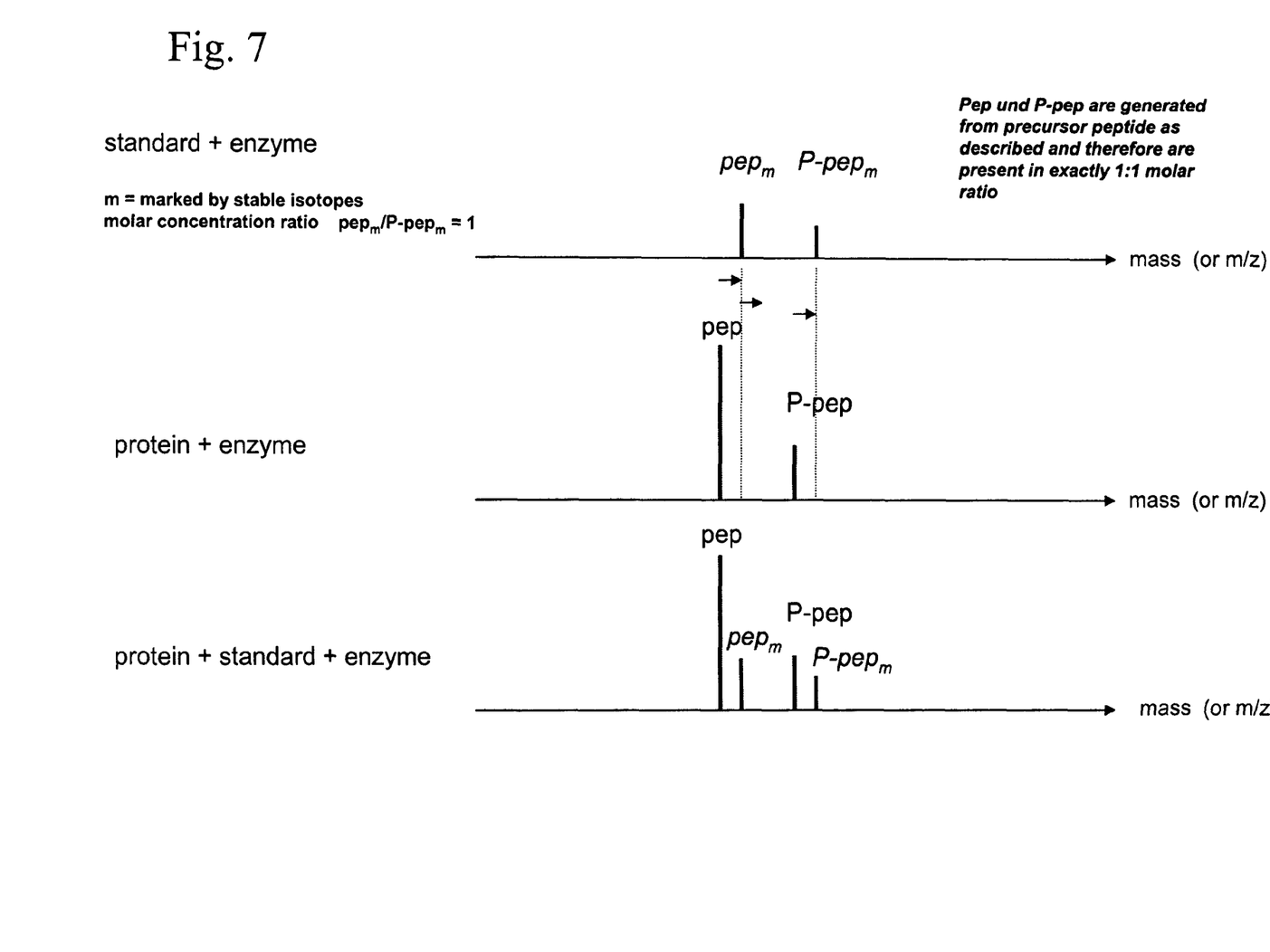
FIG. 7 shows a scheme of the determination of the ratio of a peptide and a phosphopeptide using an internal standard.

An example for the usage of an internal standard is shown in FIG. 7. The labelled peptide ($pep_m$) and the labelled phosphopeptide ($P-pep_m$) are applied to the sample of a peptide (pep) and a phosphopeptide (P-pep) as described above. The sample is analyzed in a mass spectrometer and the rate of phosphorylation of the sample is calculated using the aforementioned formulae 1 to 5.

The invention claimed is:

1. A method for determining the ratio of two distinct target-peptides or -polynucleic acids comprising:
   (a) obtaining a sample containing said two distinct target-peptides or polynucleic acids,
   (b) providing a precursor-peptide or precursor-polynucleic acid, comprising the two distinct target-peptides or -polynucleic acids in a known ratio, wherein the two distinct target-peptides or polynucleic acids are connected by a cleavage site,
   (c) cleaving the precursor-peptide or precursor-polynucleic acid at the cleavage site to obtain a standard with the known ratio of the two distinct target-peptides or polynucleic acids,
   (d) detecting a signal of each distinct target-peptide or polynucleic acid of the standard in an analyzer, comparing the signals with the known ratio and determining a correction factor,
   (e) detecting the signal of each distinct target-peptide or polynucleic acid of the sample in the analyzer and
   (f) determining the ratio of the two distinct target-peptides or -polynucleic acids by means of the correction factor.

2. A method according to claim 1, wherein the precursor-peptide or precursor-polynucleic acid is cleaved by enzymatic digestion.

3. A method according to claim 1, wherein the precursor-peptide or precursor-polynucleic acid is cleaved by chemical cleavage.

4. A method according to claim 1, wherein a stable isotope marked precursor is provided.

5. A method according to claim 4, wherein the stable isotope marked precursor is added to the sample subsequent to step (c) and the signal of the distinct target-peptides of the standard and the sample are detected in an analyzer simultaneously.

6. A method according to claim 4, wherein the ratio of the two distinct target-peptides or -polynucleic acids is determined by double ratio calculation to eliminate the compound-specific correction factors.

7. A method according to claim 1, wherein the analyzer is a mass analyzer.

8. A method according to claim 7, wherein the mass spectrometer comprises an upstream chromatographic device.

9. A method according to claim 1, wherein the analyzer is a chromatographic-device.

10. A method according to claims 1, wherein the analyzer is a fluorescence-spectrometer.

11. A method according to claim 1, wherein the analyzer detects the radioactivity.

12. A method according to claim 1, wherein the two distinct peptides or polynucleic acids are isoforms.

13. A method according to claim 12, wherein the isoforms differ from each other by a phosphorylation.

* * * * *